US012367966B2

United States Patent
Gao et al.

(10) Patent No.: US 12,367,966 B2
(45) Date of Patent: Jul. 22, 2025

(54) PREDICTING GEOGRAPHIC ATROPHY GROWTH RATE FROM FUNDUS AUTOFLUORESCENCE IMAGES USING DEEP NEURAL NETWORKS

(71) Applicant: Genentech, Inc., South San Francisco, CA (US)

(72) Inventors: Simon Shang Gao, San Francisco, CA (US); Neha Sutheekshna Anegondi, Fremont, CA (US)

(73) Assignee: Genentech, Inc., South San Francisco, CA (US)

( * ) Notice: Subject to any disclaimer, the term of this patent is extended or adjusted under 35 U.S.C. 154(b) by 299 days.

(21) Appl. No.: 18/153,762

(22) Filed: Jan. 12, 2023

(65) Prior Publication Data

US 2023/0154595 A1     May 18, 2023

Related U.S. Application Data

(63) Continuation of application No. PCT/US2021/041697, filed on Jul. 14, 2021.

(60) Provisional application No. 63/149,073, filed on Feb. 12, 2021, provisional application No. 63/052,292, filed on Jul. 15, 2020.

(51) Int. Cl.
    *G16H 50/20*     (2018.01)
    *G16H 30/40*     (2018.01)
    *G06T 3/4046*     (2024.01)

(52) U.S. Cl.
    CPC ............. *G16H 30/40* (2018.01); *G16H 50/20* (2018.01); *G06T 3/4046* (2013.01)

(58) Field of Classification Search
    None
    See application file for complete search history.

(56) References Cited

U.S. PATENT DOCUMENTS

2016/0345819 A1\*    12/2016   Jayasundera ............. G06T 7/12

FOREIGN PATENT DOCUMENTS

| EP | 3706136 A1 | 9/2020 |
|----|------------|--------|
| JP | 2019-531817 A | 11/2019 |
| JP | 2020-048703 A | 4/2020 |
| WO | 2021/113672 A1 | 6/2021 |

OTHER PUBLICATIONS

International Search Report and Written Opinion mailed on Oct. 29, 2021 in International Application No. PCT/US2021/041697, 13 pages.

(Continued)

*Primary Examiner* — Haris Sabah
(74) *Attorney, Agent, or Firm* — Haynes and Boone, LLP

(57) ABSTRACT

A method and system for evaluating geographic atrophy in a retina. A set of fundus autofluorescence (FAF) images of the retina is received. An input is generated for a machine learning system using the set of fundus autofluorescence images. A lesion area is predicted, via the machine learning system, for the geographic atrophy lesion in the retina using the set of fundus autofluorescence images. A lesion growth rate is predicted, via the machine learning system, for the geographic atrophy lesion in the retina using the input.

20 Claims, 14 Drawing Sheets

(56) References Cited

OTHER PUBLICATIONS

International Preliminary Report on Patentability dated Jan. 17, 2023 from International Application No. PCT/US2021/041697, 9 pages.

Zhang et al., "A Multi-Scale Deep Convolutional Neural Network for Joint Segmentation and Prediction of Geographic Atrophy in SD-OCT Images," 2019 IEEE 16th International Symposium on Biomedical Imaging (ISBI 2019), Apr. 8, 2019, pp. 565-568.

Holz et al., "Efficacy and Safety of Lampalizumab for Geographic Atrophy Due to Age-Related Macular Degeneration: Chroma and Spectri Phase 3 Randomized Clinical Trials," JAMA Ophthalmology, 136(6), pp. 666-677 (2018).

Holekamp et al., "Natural History of Geographic Atrophy Secondary to Age-Related Macular Degeneration: Results from the Prospective Proxima A and B Clinical Trials," Ophthalmology, 127(6), pp. 769-783 (2020).

Flaxman et al., "Global Causes of Blindness and Distance Vision Impairment 1990-2020: A Systematic Review and Meta-Analysis," Lancet Glob Health, 5(12), e1221-e1234 (2017).

Clemons et al., "Risk Factors for the Incidence of Advanced Age-Related Macular Degeneration in the Age-Related Eye Disease Study (AREDS) AREDS report No. 19," Ophthalmology, 112(4), pp. 533-539 (2005).

Boyer et al., "The Pathophysiology of Geographic Atrophy Secondary to Age-Related Macular Degeneration and the Complement Pathway as a Therapeutic Target," Retina, 37(5), pp. 819-835 (2017).

Vingerling et al., "The Prevalence of Age-Related Maculopathy in the Rotterdam Study," Ophthalmology, 102(2), pp. 205-210 (1995).

Sunness, "The Natural History of Geographic Atrophy, the Advanced Aatrophic Form of Age-Related Macular Degeneration," Molecular Vision, 5:25 (1999), 5 pages.

Klein et al., "The Relationship of Cardiovascular Disease and Its Risk Factors to Age-Related Maculopathy. The Beaver Dam Eye Study," Ophthalmology, 100(3), pp. 406-414 (1993).

Fleckenstein et al., "The Progression of Geographic Atrophy Secondary to Age-Related Macular Degeneration," American Academy of Ophthalmology, 125(3), pp. 369-390 (2018).

Nebbioso et al., "Therapeutic Approaches with Intravitreal Injections in Geographic Atrophy Secondary to Age-Related Macular Degeneration: Current Drugs and Potential Molecules," International Journal of Molecular Sciences, 20(7), 2019, 14 pages.

Gobel et al., "Imaging Geographic Atrophy in Age-Related Macular Degeneration," Ophthalmologica, 226(4), pp. 182-190 (2011).

Schmitz-Valckenberg et al., "Fundus Autofluorescence Imaging: Review and Perspectives." Retina 2008, 28(3), pp. 385-409.

Holz et al., "Imaging Protocols in Clinical Studies in Advanced Age-Related Macular Degeneration: Recommendations from Classification of Atrophy Consensus Meetings," American Academy of Ophthalmology, 124(4), pp. 464-478 (2017).

Schmitz-Valckenberg et al., "Semiautomated Image Processing Method for Identification and Quantification of Geographic Atrophy in Age-Related Macular Degeneration," Investigative Ophthalmology & Visual Science, 52(10), pp. 7640-7646 (2011).

Pfau et al., "Prognostic Value of Shape-Descriptive Factors for the Progression of Geographic Atrophy Secondary to Age-Related Macular Degeneration," Retina, 39(8), pp. 1527-1540 (2019), 30 pages.

Holmen et al., "Precursors and Development of Geographic Atrophy with Autofluorescence Imaging: Age-Related Eye Disease Study 2 Report No. 18," American Academy of Ophthalmology, Retina, 3(9), pp. 724-733 (2019).

Batioglu et al., "Geographic Atrophy Progression in Eyes with Age-Related Macular Degeneration: Role of Fundus Autofluorescence Patterns, Fellow Eye and Baseline Atrophy Area," Ophthalmic Research, 52(2), pp. 53-59 (2014).

Schmitz-Valckenberg et al., "Natural History of Geographic Atrophy Progression Secondary to Age-Related Macular Degeneration (Geographic Atrophy Progression Study)," American Academy of Ophthalmology, Ophthalmology 123(2), pp. 361-368 (2016).

Bearelly et al., "Use of Fundus Autofluorescence Images to Predict Geographic Atrophy Progression," Retina, 31(1), pp. 81-86 (2011).

Normand et al., Prediction of Geographic Atrophy Progression by Deep Learning Applied to Retinal Imaging, Investigative Ophthalmology & Visual Science, (2019), 1 page.

Anegondi et al., "Evaluation of Shape-Descriptive and Texture Features as Potential Prognostic Variables in Progression of Geographic Atrophy," Investigative Ophthalmology & Visual Science, 60(9), 1906-1906 (2019).

Friesenhahn et al., "Initial Lesion Growth Rates and Other Baseline Prognostic Factors Can Improve the Design of Clinical Trials in Geographic Atrophy (GA)," Investigative Ophthalmology & Visual Science, 61(7), 2988-2988 (2020).

Ruder, "An Overview of Multi-Task Learning in Deep Neural Networks," (2017), https://arxiv.org/abs/1706.05098, 14 pages.

Szegedy et al., "Rethinking the Inception Architecture for Computer Vision," 2016 IEEE Conference on Computer Vision and Pattern Recognition (CVPR), 2818-2826 (2016), 10 pages.

Cheung et al., "Age-Related Macular Degeneration," Pharmacotherapy, 33(8), pp. 838-855 (2013).

Sadda et al., "Consensus Definition for Atrophy Associated with Age-Related Macular Degeneration on OCT: Classification of Atrophy Report 3," American Academy of Ophthalmology, Ophthalmology, 125(4), pp. 537-548 (2018).

Anegondi et al., "Predicting Geographic Atrophy Growth Rate from Fundus Autofluorescence Images Using Deep Neural Networks," 6 pages.

\* cited by examiner

|  | | Model (Inner folds, 5-fold CV) ~ Fold 1 ($R^2$ mean [SD]) | ~ Fold 2 ($R^2$ mean [SD]) | ~ Fold 3 ($R^2$ mean [SD]) | ~ Fold 4 ($R^2$ mean [SD]) | ~ Fold 5 ($R^2$ mean [SD]) |
|---|---|---|---|---|---|---|
| Lesion growth rate | FAF | 0.92 [0.02] | 0.94 [0.01] | 0.92 [0.02] | 0.91 [0.02] | 0.92 [0.03] |
| | Model (Outer folds) Fold 1 ($R^2$ mean [CI]) | Fold 2 ($R^2$ mean [CI]) | Fold 3 ($R^2$ mean [CI]) | Fold 4 ($R^2$ mean [CI]) | Fold 5 ($R^2$ mean [CI]) | |
| | FAF | 0.94 [0.91 - 0.97] | 0.88 [0.75 - 0.96] | 0.94 [0.92 - 0.96] | 0.95 [0.93 - 0.96] | 0.96 [0.95 - 0.97] |
| Lesion area | Model (Inner folds, 5-fold CV) ~ Fold 1 ($R^2$ mean [SD]) | ~ Fold 2 ($R^2$ mean [SD]) | ~ Fold 3 ($R^2$ mean [SD]) | ~ Fold 4 ($R^2$ mean [SD]) | ~ Fold 5 ($R^2$ mean [SD]) | |
| | FAF | 0.43 [0.03] | 0.46 [0.02] | 0.45 [0.03] | 0.48 [0.05] | 0.45 [0.05] |
| | Model (Outer folds) Fold 1 ($R^2$ mean [CI]) | Fold 2 ($R^2$ mean [CI]) | Fold 3 ($R^2$ mean [CI]) | Fold 4 ($R^2$ mean [CI]) | Fold 5 ($R^2$ mean [CI]) | |
| | FAF | 0.55 [0.46 - 0.65] | 0.43 [0.31 - 0.54] | 0.51 [0.41 - 0.62] | 0.41 [0.30 - 0.52] | 0.50 [0.40 - 0.60] |

FIG. 13

PREDICTING GEOGRAPHIC ATROPHY GROWTH RATE FROM FUNDUS AUTOFLUORESCENCE IMAGES USING DEEP NEURAL NETWORKS

CROSS-REFERENCE TO RELATED APPLICATIONS

This application is a continuation of International Application No. PCT/US2021/041697 filed Jul. 14, 2021, which claims priority to U.S. Provisional Patent Application No. 63/149,073 filed Feb. 12, 2021, entitled "Predicting Geographic Atrophy Growth Rate from Fundus Autofluorescence Images using Deep Neural Networks," and to U.S. Provisional Patent Application No. 63/052,292, filed Jul. 15, 2020, entitled "Predicting Geographic Atrophy Growth Rate from Fundus Autofluorescence Images using Deep Neural Networks," each of which is incorporated herein by reference in its entirety.

FIELD

This description is generally directed towards evaluating geographic atrophy in a retina. More specifically, this description provides methods and systems for predicting a growth rate for a geographic atrophy lesion using images from multiple modalities such as, for example, fundus autofluorescence (FAF) images and optical coherence tomography (OCT) images.

BACKGROUND

Age-related macular degeneration (AMD) is a leading cause of vision loss in patients 50 years or older. Geographic atrophy (GA) is a late-stage form of AMD. GA is the degeneration of the retina and can hinder daily activities such as, for example, driving, reading, etc. GA is characterized by progressive and irreversible loss of choriocapillaries, retinal pigment epithelium (RPE), and photoreceptors. GA progression varies between patients and currently, no widely accepted treatment for preventing or slowing down the progression of GA exists. Therefore, evaluating GA progression in individual patients may be important to researching GA and developing an effective treatment. Currently, the diagnosis and monitoring of GA lesion enlargement may be performed using fundus autofluorescence (FAF) images that are obtained by confocal scanning laser ophthalmoscopy (cSLO). On FAF images, regions of GA can be seen as dark areas and GA progression may be evaluated based on the rate of increase of those dark areas over time. Currently available techniques for evaluating GA progression using an FAF image rely on human graders to perform manual steps that require knowledge and expertise and that take time. Further, because of the variability in human grading, there may be differences between how a first grader looks at an FAF image as compared to a second grader. This variability may skew the results. A desire exists to more consistently, reliably, and expediently evaluate GA progression.

SUMMARY

In one or more embodiments, a method and system for evaluating geographic atrophy in a retina are provided. A set of fundus autofluorescence (FAF) images of the retina is received. An input is generated for a machine learning system using the set of fundus autofluorescence images. A lesion area is predicted, via the machine learning system, for the geographic atrophy lesion in the retina using the set of fundus autofluorescence images. A lesion growth rate is predicted, via the machine learning system, for the geographic atrophy lesion in the retina using the input.

In one or more embodiments, a method and system for evaluating geographic atrophy in a retina are provided. A set of fundus autofluorescence (FAF) images of the retina is received. An input is generated for a machine learning system using the set of fundus autofluorescence images. A lesion area is predicted, via the machine learning system, for a geographic atrophy lesion in the retina using the input. A lesion growth rate is predicted, via the machine learning system, for the geographic atrophy lesion using the lesion area predicted by the machine learning system.

In one or more embodiments, a method for predicting a lesion growth rate for a geographic atrophy lesion is provided. A set of fundus autofluorescence images are accessed at a computing system. A geographic atrophy progression metric is derived from the set of fundus autofluorescence images. A fundus autofluorescence image of a subject is accessed. A lesion area that is subject-specific for a geographic atrophy lesion of the subject is predicted, from the fundus autofluorescence image and the geographic atrophy progression metric. A subject-specific prediction of lesion growth rate is output from the predicted geographic atrophy lesion area.

In one or more embodiments, a system comprises one or more data processors; and a non-transitory computer readable storage medium containing instructions which, when executed on the one or more data processors, cause the one or more data processors to perform the method of any one of the embodiments described herein.

In one or more embodiments, a computer-program product is provided that is tangibly embodied in a non-transitory machine-readable storage medium and that includes instructions configured to cause one or more data processors to perform the method of any one of the embodiments described herein.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 13 is a table illustrating the training performance of a multitask model in predicting both lesion growth rate and lesion area in accordance with various embodiments.

Figure 1:
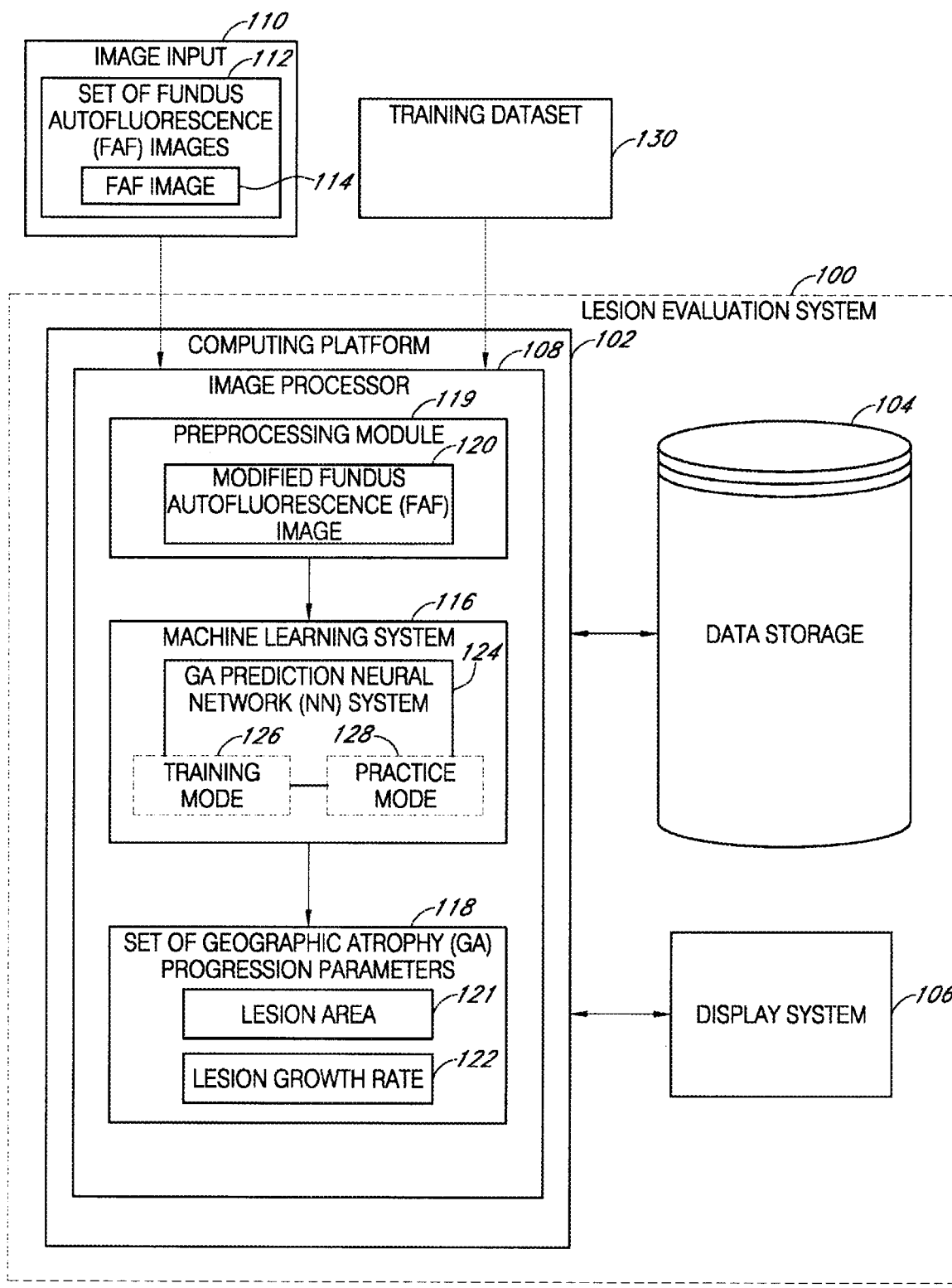
FIG. 1 is a block diagram of a lesion evaluation system in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

I. Overview

The ability to accurately predict geographic atrophy (GA) progression based on baseline assessments may be useful in many different scenarios. As one example, predictions about GA progression may be used to improve patient stratification in clinical trials where the goal is to slow GA progression, thereby allowing for improved assessment of treatment effects. Additionally, in some cases, predictions about GA progression may be used to understand disease pathogenesis via correlation to genotypic or phenotypic signatures.

A GA lesion can be imaged by various imaging modalities. Fundus autofluorescence (FAF) images have been used to quantify the GA lesion area. GA growth rate, which is the change in lesion area over some time period, as measured using FAF images, is widely accepted as an anatomic metric for GA progression in clinical trials. In present embodiments, GA growth rate (e.g., annualized growth rate) may be predicted from baseline FAF images.

Currently available techniques for evaluating GA progression using an FAF image rely on human graders to first manually identify the portion of an FAF image that is the GA lesion. In some cases, this first step is semi-automated, relying on the human grader to make manual refinements and/or corrections to a software-generated initial outline of the GA area. Then, the identified portion of the FAF image is evaluated to determine the GA lesion area and GA growth rate. Thus, these techniques may involve a two-step process that can take more time than is desirable, may be prone to human error, may be less accurate than desired, and/or may produce variable results depending on the knowledge and expertise of one or human graders. Accordingly, a desire exists for methods and systems that improve the speed, efficiency, and accuracy associated with predicting GA lesion area or GA growth rate.

The embodiments herein provide the desired improvements in speed, efficiency, and accuracy associated with predicting GA lesion area, GA growth rate, or both, for research and clinical settings. In particular, the various embodiments described herein provide methods and systems for automatically predicting a set of GA progression metrics (e.g., GA growth rate, GA lesion area, or both) using baseline FAF images and a machine learning system. For example, for a given subject, the machine learning system uses deep learning that has been trained to automatically predict the set of GA progression metrics from a baseline FAF image of the subject's retina. The machine learning system is trained using a training dataset derived from multiple studies sharing the same or similar inclusion criteria. Training with this type of training dataset improves the predictive performance of the machine learning system. For example, using such a trained machine learning system to analyze FAF images (e.g., baseline FAF images) and automatically predict one or more GA progression metrics may improve the speed and efficiency of making these predictions, as well as the accuracy of these predictions. Thus, the embodiments described herein provide a fully automated methodology and system for predicting GA lesion area at some future point in time, GA growth rate (e.g., annualized growth rate), or both based on a baseline FAF image input into a machine learning system that uses deep learning, trained as described herein.

In various embodiments, a machine learning system that uses deep learning can be used to generate accurate predictions for the progression of GA lesions over time from baseline FAF images. For example, one or more baseline FAF images of a retina of a subject may be processed using a deep learning system that automatically outputs a predicted lesion area for a GA lesion in the retina, a predicted lesion growth rate for the GA lesion, or both. In some cases, the lesion growth rate is predicted based on predictions of lesion area. For example, two or more predictions of lesion area for two or more different points in time, respectively, may be used to predict lesion growth rate.

The predicted lesion area and/or predicted lesion growth rate may have an accuracy that can be successfully relied upon for use in clinical practice. For example, one or more predicted GA progression metrics can be used to determine whether a subject is a candidate for a clinical trial, to which clinical trial to assign the subject, how to customize a treatment for the subject, how to monitor the progress of the subject during the clinical trial, or a combination thereof.

The machine learning system (e.g., a deep learning system) used to predict GA progression metrics based on FAF images may be trained using a dataset that ensures the desired level of prediction accuracy. For example, the training dataset may be compiled from multiple studies that have the same (or substantially same or similar) inclusion criteria (e.g., subjects with bilateral GA). Ensuring that the training dataset is built from studies that share the same (or substantially same or similar) inclusion criteria helps ensure a certain type of consistency across the FAF images that will improve training accuracy and thereby, prediction accuracy as compared to using training data from studies with different kinds of inclusion criteria. In some embodiments, the machine learning system may be selected or configured such that the total amount of time, processing resources, or both used for training is reduced.

Thus, various embodiments described herein relate to a GA progression prediction methodologies and systems.

These GA progression prediction methodologies and systems may be used to predict lesion area, lesion growth rate, or both for a GA lesion identified in the retina of a subject. The techniques described herein can be used to predict the prognosis of one or more subjects, predict the responsiveness of one or more subjects to various treatments, identify the treatment predicted to be effective for an individual subject, assign one or more subjects into an appropriate arm within a clinical trial, or a combination thereof.

The lesion area, lesion growth rate, or both predicted using the methodologies and/or systems described herein may be used to generate an output that includes an indication of whether a subject is eligible for a clinical trial for testing a medical treatment for geographic atrophy. In some embodiments, this output may be used to enroll the subject in the clinical trial, exclude the subject from participating in the clinical trial, customize a protocol in the clinical trial for the subject, or enroll the subject in a different clinical trial.

II. Geographic Atrophy (GA) Lesion Evaluation

Referring now to the figures, FIG. 1 is a block diagram of a lesion evaluation system 100 in accordance with various embodiments. Lesion evaluation system 100 is used to evaluate geographic atrophy (GA) lesions in the retinas of subjects. Lesion evaluation system 100 includes computing platform 102, data storage 104, and display system 106. Computing platform 102 may take various forms. In one or more embodiments, computing platform 102 includes a single computer (or computer system) or multiple computers in communication with each other. In other examples, computing platform 102 takes the form of a cloud computing platform.

Data storage 104 and display system 106 are each in communication with computing platform 102. In some examples, data storage 104, display system 106, or both may be considered part of or otherwise integrated with computing platform 102. Thus, in some examples, computing platform 102, data storage 104, and display system 106 may be separate components in communication with each other, but in other examples, some combination of these components may be integrated together.

Lesion evaluation system 100 includes image processor 108, which may be implemented using hardware, software, firmware, or a combination thereof. In one or more embodiments, image processor 108 is implemented in computing platform 102. Image processor 108 receives image input 110 for processing. For example, image input 110 may be sent as input into image processor 108, retrieved from data storage 104 or some other type of storage (e.g., cloud storage), or received in some other manner.

Image input 110 may include one or more images obtained for one or more subjects. Image input 110 includes set of fundus autofluorescence (FAF) images 112. Set of FAF images 112 includes one or more FAF images, each of which captures a retina of a subject. The retina of a subject may have a geographic atrophy (GA) lesion. This GA lesion may be a continuous or discontinuous region of the retina that has suffered degeneration (e.g., chronic progressive degeneration). The GA lesion may include one lesion (e.g., one continuous lesion region) or multiple lesions (e.g., discontinuous lesion region comprised of multiple, separate lesions).

In one or more embodiments, set of FAF images 112 includes one or more baseline FAF images that are captured at a baseline (or reference) point in time. The baseline (or reference) point in time may be, for example, a point in time prior to treatment, the same day as a treatment dose (e.g., a first treatment dose), or some other type of baseline or reference point in time. FAF image 114 is one example of an FAF image in set of FAF images 112. FAF image 114 is a baseline FAF image that captures a GA lesion.

In various embodiments, image processor 108 processes image input 110 (e.g., set of FAF images 112) using machine learning system 116 to predict set of GA progression parameters 118 corresponding to a GA lesion. For example, machine learning system 116 may receive FAF image 114 as input and process FAF image 114 to predict set of GA progression parameters 118 for the GA lesion captured in FAF image 114. In other examples, preprocessing module 119 is used to preprocess image input 110 prior to sending image input 110 into machine learning system 116. For example, preprocessing module 119 may preprocess FAF image 114 to form modified FAF image 120 that is sent into machine learning system 116. The preprocessing may include resizing, normalization of image intensities (e.g., pixel intensities), or a combination thereof. The resizing may include resizing FAF image 114 into a selected pixel by pixel size (e.g., 512 pixels by 512 pixels). The normalization of image intensities may include normalizing the intensity values of the pixels in FAF image 114 to a selected scale (e.g., a scale from 0 to 1, a scale from −1 to 1, or another type of scale).

Set of GA progression parameters 118 generated by machine learning system 116 may include, for example, lesion area 121, lesion growth rate 122, or both corresponding to the GA lesion. Lesion area 121 may refer to an area covered by the GA lesion, whether the GA lesion is a continuous region or a discontinuous region. In some embodiments, lesion area 121 may be generated in units millimeter squared ($mm^2$). Lesion area 121 may be the lesion area estimated for the baseline point in time. In other examples, lesion area 121 is the lesion area predicted for a point time after the baseline point in time. For example, lesion area 121 includes the area of the GA lesion as predicted for 3 months, 6 months, 9 months, one year, or some other interval of time after the baseline point in time. In still other examples, lesion area 121 includes multiple predictions for multiple points in time after the baseline point in time.

Lesion growth rate 122 may be a longitudinal change in the lesion area of the GA lesion. In other words, the lesion growth rate 122 may be the predicted change in lesion area over time. In some cases, this growth rate may be an annualized growth rate (e.g., $mm^2$/year).

Machine learning system 116, which may be also referred to as a machine learning model, may be implemented in any of a number of different ways. In one or more embodiments, machine learning system 116 is implemented using a deep learning system. For example, machine learning system 116 may be implemented using GA Prediction Neural Network (NN) System 124 that uses deep learning. GA Prediction NN System 124 may include any number of or combination of neural networks. In one or more embodiments, GA Prediction NN System 124 takes the form of a convolutional neural network (CNN) system that includes one or more neural networks. Each of these one or more neural networks may itself be a convolutional neural network. In some cases, GA Prediction NN System 124 includes multiple subsystems and/or layers, each including one or more neural networks.

Machine learning system 116 may be used in either training mode 126 or prediction mode 128. In training mode 126, machine learning system 116 is trained using training dataset 130. Training dataset 130 includes an FAF image dataset that is selected to ensure machine learning system 116 can be used in prediction mode 128 with the desired level of accuracy. In one or more embodiments, training dataset 130 includes FAF images obtained via one or more studies (e.g., clinical studies, research studies, etc.). When the FAF images are obtained from multiple studies, the studies are selected such that the inclusion criteria for the studies are the same. Ensuring that the same inclusion criteria were used in the studies helps ensure a certain type of consistency across the FAF images that will improve training accuracy and thereby, prediction accuracy. In various embodiments, training dataset 130 includes FAF images for subjects that have bilateral geographic atrophy.

Figure 2:
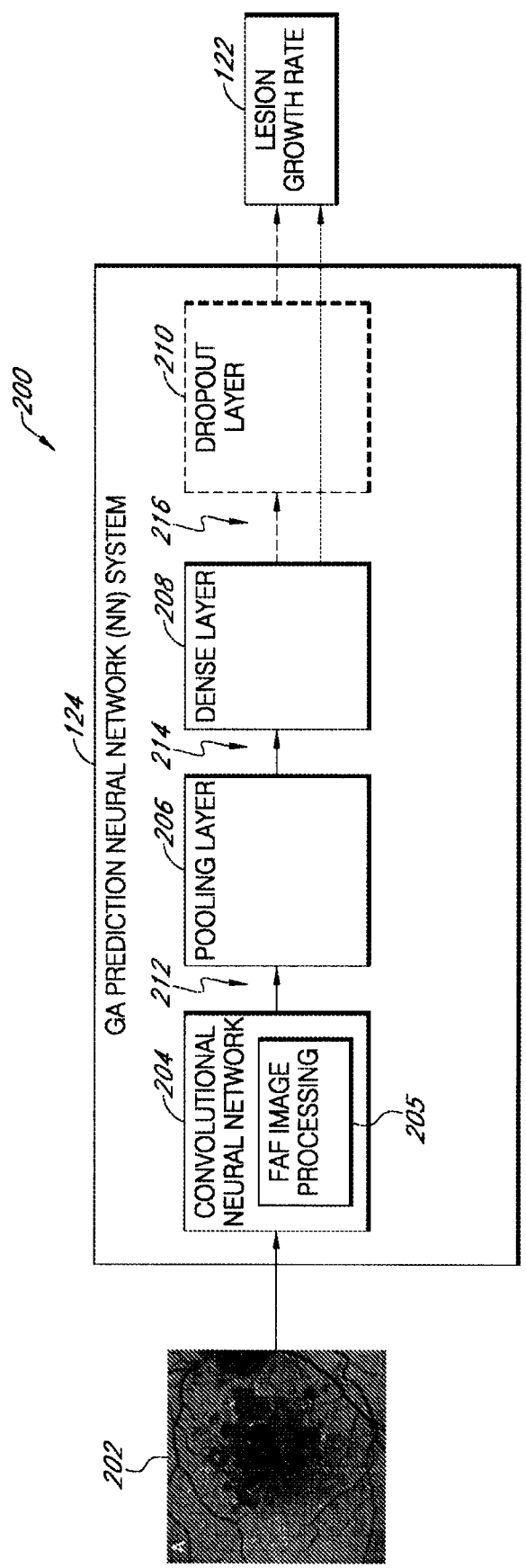
FIG. 2 is a block diagram of the neural network system from FIG. 1 having a base architecture in accordance with various embodiments.
Figure 3:
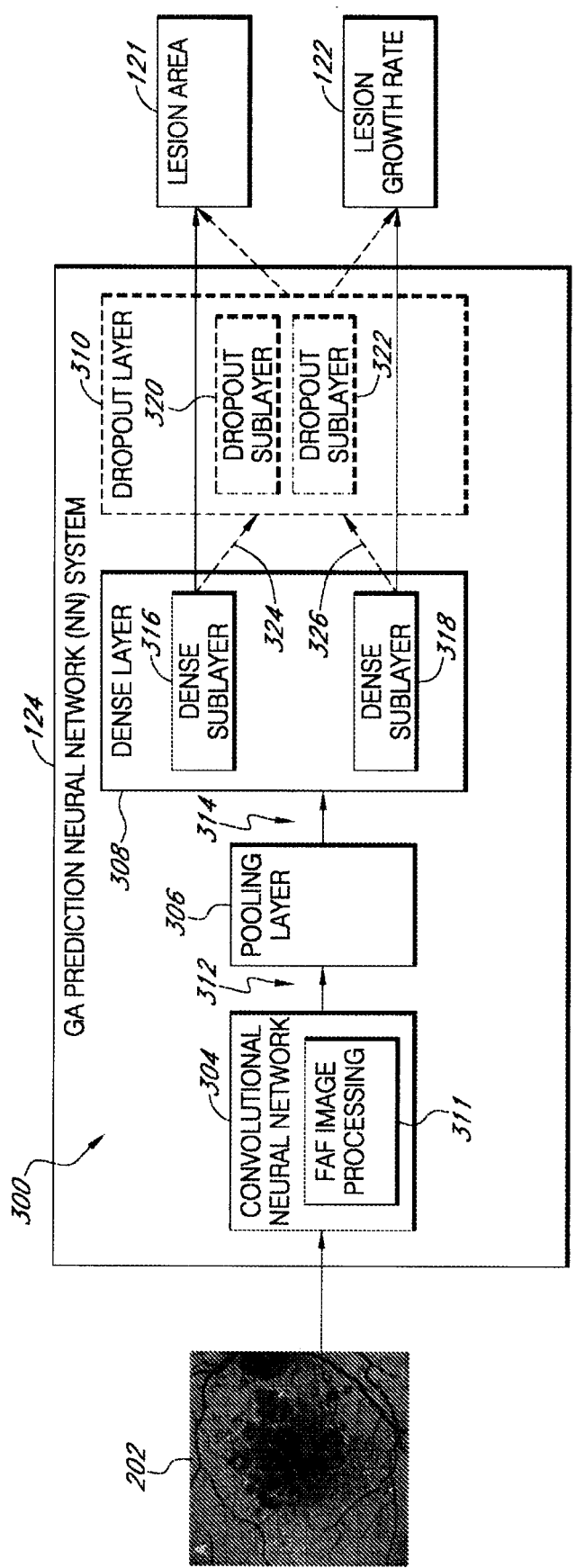
FIG. 3 is a block diagram of the neural network system from FIG. 1 having a multitask architecture in accordance with various embodiments.
Figure 4:
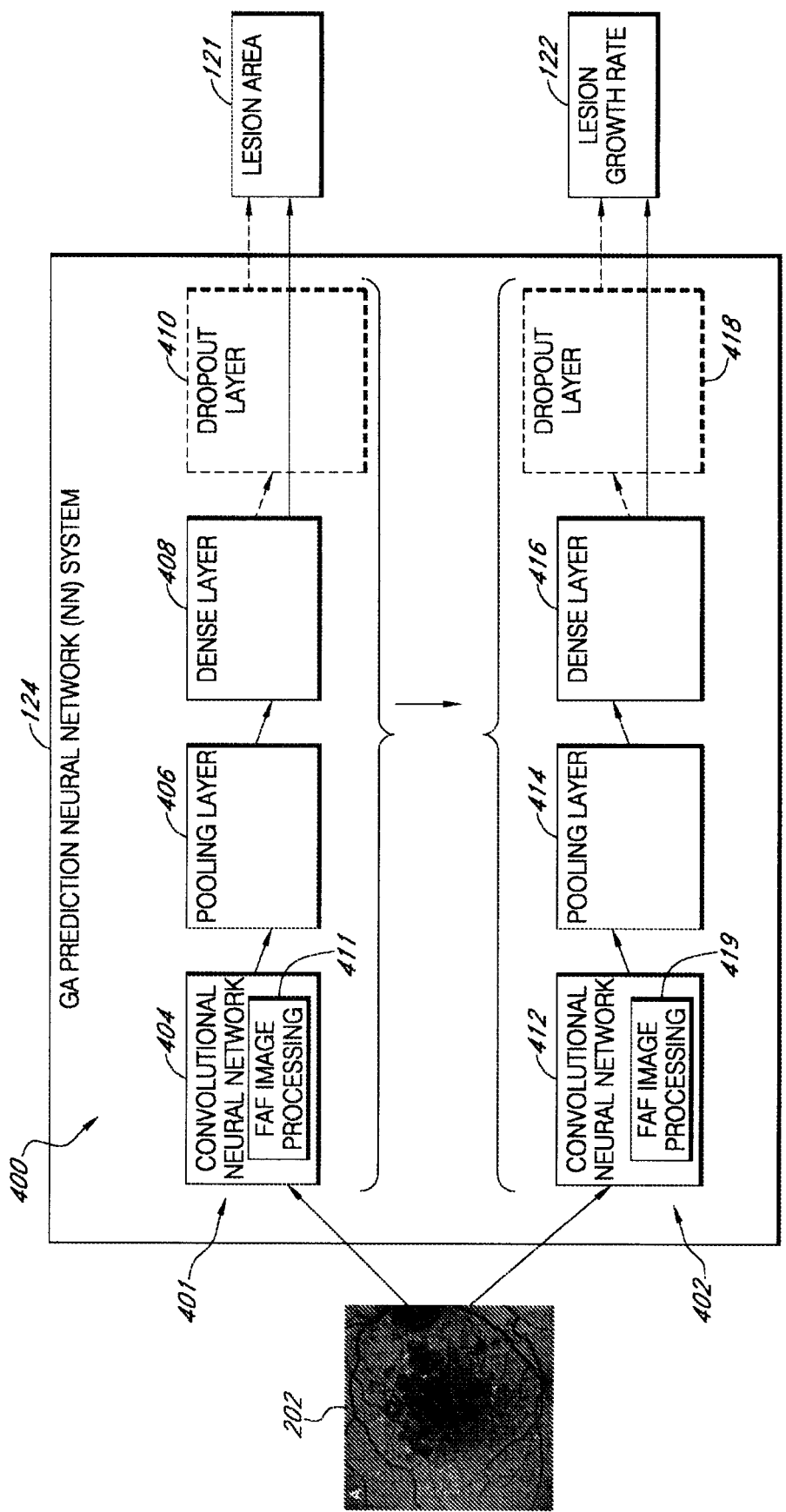
FIG. 4 is a block diagram of the neural network system from FIG. 1 having a cascade architecture in accordance with various embodiments.

FIGS. 2-4 are block diagrams illustrating various architectures or configurations for GA Prediction NN System 124 in FIG. 1. FIGS. 2-4 are described with ongoing reference to lesion evaluation system 100 in FIG. 1. GA Prediction NN System 124 may have various configurations for receiving FAF images as input and processing those FAF images.

FIG. 2 is a block diagram of GA Prediction NN System 124 having base architecture 200 in accordance with various embodiments. GA Prediction NN System 124 having base architecture 200 is used to receive FAF input 202, process FAF input 202, and generate lesion growth rate 122 based on FAF input 202. FAF input 202 takes the form of an FAF image, such as FAF image 114 in FIG. 1, or a preprocessed FAF image, such as modified FAF image 120 in FIG. 1.

Base architecture 200 may include, for example, without limitation, convolutional neural network 204, pooling layer 206, and dense layer 208. When used in training mode 126, base architecture 200 may also include dropout layer 210. Convolutional neural network 204 of GA Prediction NN System 124 receives FAF input 202. Convolutional neural network 204 may be comprised of any number or combination of neural networks that includes at least one convolutional neural network. Convolutional neural network 204 performs FAF image processing 205 using FAF input 202. Convolutional neural network 204 generates an output 212 that is fed into pooling layer 206. Pooling layer 206 may include one or more different and/or same pooling layers. In one or more embodiments, pooling layer 206 includes a global average pooling layer. Pooling layer 206 generates an output 214 that is sent into dense layer 208.

Dense layer 208 includes one or more different and/or same dense layers. Each of these dense layers may be comprised of a selected number of nodes. For example, a dense layer, dense (256), is comprised of 256 nodes. When in training mode 126, dense layer 208 performs one or more operations on its received input to generate an output 216 that is sent as input into dropout layer 210. Dropout layer 210 may include one or more operational dropout layers that help reduce or prevent overfitting of training dataset 130. For example, dropout layer 210 can be used to nullify the contribution of some nodes towards the final output, lesion growth rate 122. When in prediction mode 128, dropout layer 210 is not used and dense layer 208 outputs lesion growth rate 122.

In some embodiments, base architecture 200 may include one or more additional layers. For example, base architecture 200 may include a prediction layer after dropout layer 310 that outputs lesion area 121 and lesion growth rate 122. This prediction layer may be implemented using, for example, without limitation, a dense layer comprised of 1 node. In other embodiments, base architecture 200 may include a dense layer comprised of some other number of nodes.

In this manner, GA Prediction NN System 124 with base architecture 200 is able to receive FAF input 202 and, via an automated process, output lesion growth rate 122 with the desired level of accuracy. For example, GA Prediction NN System 124 may have been trained using a multitude of baseline FAF images (e.g., on a training dataset built from multiple studies sharing the same inclusion criteria) that enable GA Prediction NN System 124 to efficiently and accurately output lesion growth rate 122 based on FAF input 202.

FIG. 3 is a block diagram of GA Prediction NN System 124 having multitask architecture 300 in accordance with various embodiments. GA Prediction NN System 124 having multitask architecture 300 may receive FAF input 202 for processing. As described above, FAF input 202 may take the form of FAF image 114 or modified FAF image 120 in FIG. 1. GA Prediction NN System 124 processes FAF input 202 to generate both lesion growth rate 122 and lesion area 121. In one or more embodiments, lesion area 121 is an estimated baseline lesion area for a baseline point in time. In other embodiments, lesion area 121 is a predicted lesion area for a future point in time relative to the baseline point in time.

Multitask architecture 300 includes convolutional neural network 304, pooling layer 306, and dense layer 308. When used in training mode 126, multitask architecture 300 may also include dropout layer 310. In various embodiments, convolutional neural network 304, pooling layer 306, dense layer 308, and dropout layer 310 are implemented in a manner similar to convolutional neural network 204, pooling layer 206, dense layer 208, and dropout layer 210, respectively, in FIG. 2. However, in training mode 126, dropout layer 210 outputs both lesion area 121 and lesion growth rate 122; in prediction mode 128, dense layer 208 outputs both lesion area 121 and lesion growth rate 122.

Convolutional neural network 304 receives FAF input 202 and performs FAF image processing 311 using FAF input 202. Convolutional neural network 304 generates an output 312 that is sent into pooling layer 306. Pooling layer 306 receives output 312, performs one or more operations using output 312, and generates an output 314 that is sent into dense layer 308.

In some embodiments, dense layer 308 includes two sublayers: a first dense sublayer 316 (e.g., dense (256)) and a second dense sublayer 318 (e.g., dense (256)). Further, dropout layer 310 may also include two corresponding sublayers: a first dropout sublayer 320 and a second dropout sublayer 322. First dense sublayer 316 receives output 314 and generates an output 324 that is sent into first dropout sublayer 320. Second dense sublayer 318 receives output 314 and generates output 326 that is sent into second dropout sublayer 322. First dropout sublayer 320 outputs lesion area 121; second dropout sublayer 322 outputs lesion growth area 122.

In this manner, GA Prediction NN System 124 with multitask architecture 300 is able to receive FAF input 202 and, via an automated process, output lesion area 121 and lesion growth rate 122 with the desired level of accuracy. For example, GA Prediction NN System 124 may have been trained using a multitude of baseline FAF images (e.g., on a training dataset built from multiple studies sharing the same inclusion criteria) that enable GA Prediction NN System 124 to efficiently and accurately output lesion area 121 and lesion growth rate 122 based on FAF input 202.

FIG. 4 is a block diagram of GA Prediction NN System 124 having cascade architecture 400 in accordance with various embodiments. GA Prediction NN System 124 having cascade architecture 400 may receive FAF input 202 for processing. As described above, FAF input 202 may take the form of FAF image 114 or modified FAF image 120 in FIG. 1. GA Prediction NN System 124 processes FAF input 202 to generate both lesion growth rate 122 and lesion area 121. In one or more embodiments, lesion area 121 is an estimated baseline lesion area for a baseline point in time. In other embodiments, lesion area 121 is a predicted lesion area for a future point in time relative to the baseline point in time.

Cascade architecture 400 includes area subsystem 401 and growth rate subsystem 402. Area subsystem 401 is trained to output lesion area 121; growth rate subsystem 402 is trained to output lesion growth rate 122. In training mode 126, area subsystem 401 may be trained first and its parameters (e.g., weights) used to train growth rate subsystem 402. In prediction mode 128, lesion area 121 predicted by area subsystem 401 may be used in growth rate subsystem 402 to predict lesion growth rate 122.

Area subsystem 401 includes convolutional neural network 404, pooling layer 406, and dense layer 408. When used in training mode 126, area subsystem 401 may also include dropout layer 410. In various embodiments, convolutional neural network 404, pooling layer 406, dense layer 408, and dropout layer 410 are implemented in a manner similar to convolutional neural network 204, pooling layer 206, dense layer 208, and dropout layer 210, respectively, in FIG. 2. For example, convolutional neural network 404 may receive FAF input 202 and perform FAF image processing 411 to generate an output that is sent into pooling layer 406, which sends an output to dense layer 408. In prediction mode 128, dense layer 408 outputs lesion area 121. But in training mode 126, dense layer 408 sends an output to dropout layer 410, which outputs lesion area 121.

Growth rate subsystem 402 includes convolutional neural network 412, pooling layer 414, and dense layer 416. When used in training mode 126, growth rate subsystem 402 may also include dropout layer 418. In various embodiments, convolutional neural network 412, pooling layer 414, dense layer 416, and dropout layer 410 are implemented in a manner similar to convolutional neural network 204, pooling layer 206, dense layer 208, and dropout layer 210, respectively, in FIG. 2. For example, convolutional neural network 412 may receive FAF input 202 and perform FAF image processing 419 to generate an output that is sent into pooling layer 414, which sends an output to dense layer 408. In prediction mode 128, dense layer 416 outputs lesion growth rate 122 using lesion area 121 predicted by area subsystem 401. In training mode 126, dense layer 416 sends an output to dropout layer 418, which outputs lesion growth rate 122 that has been determined using lesion area 121 predicted by area subsystem 401.

With cascade architecture 400, pre-trained neural network parameters (e.g., weights) of area subsystem 401 may be fine-tuned through training to enable area subsystem 401 to predict lesion area 121 with the desired level of accuracy. The parameters of growth rate subsystem 402 may then be fine-tuned using the tuned parameters of area subsystem 401 to enable growth rate subsystem 402 to predict lesion growth rate 122 with the desired level of accuracy.

In some embodiments, this type of cascade path approach is only used in training mode 126. Once GA Prediction NN System 124 has been trained via the cascade path approach, FAF input 202 may be fed into area subsystem 401 and growth rate subsystem 402, each of which may be independently capable of predicting its corresponding GA progression parameter.

In this manner, GA Prediction NN System 124 with cascade architecture 400 is able to receive FAF input 202 and, via an automated process, output lesion area 121 and lesion growth rate 122 with the desired level of accuracy. For example, GA Prediction NN System 124 may have been trained using a multitude of baseline FAF images (e.g., on a training dataset built from multiple studies sharing the same inclusion criteria) that enable GA Prediction NN System 124 to efficiently and accurately output lesion area 121 and lesion growth rate 122 based on FAF input 202.

The base architecture 200 in FIG. 2, multitask architecture 300 in FIG. 3, and cascade architecture 400 in FIG. 4 are examples of architectures or configurations for GA Prediction NN System 124 in FIG. 1. In other embodiments, however, GA Prediction NN System 124 may have some other type of architecture or configuration.

Figure 5:
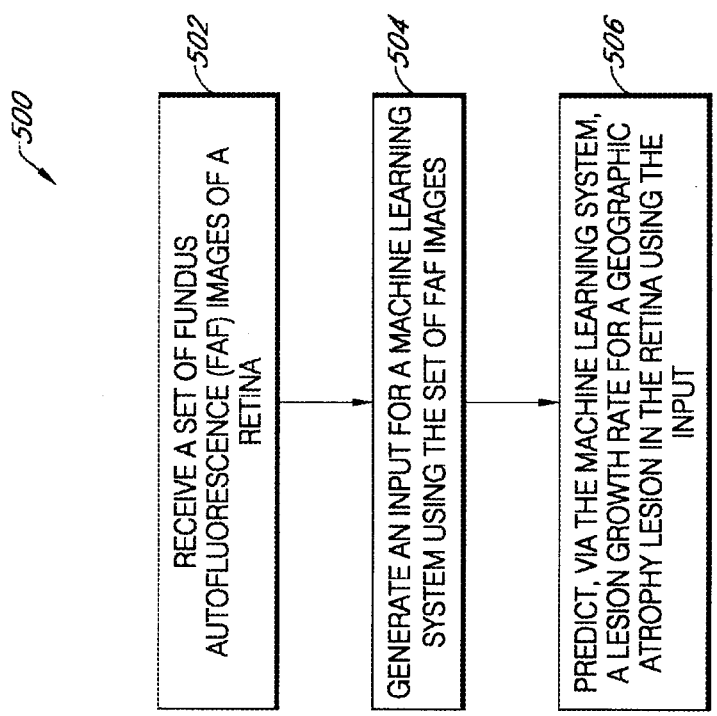
FIG. 5 is a flowchart of a process for evaluating a geographic atrophy lesion in accordance with various embodiments.

FIG. 5 is a flowchart of a process 500 for evaluating a geographic atrophy lesion in accordance with various embodiments. In various embodiments, process 500 is implemented using the lesion evaluation system 100 described in FIG. 1. In particular, process 500 may be used to predict set of GA progression parameters 118 in FIG. 1.

Step 502 includes receiving a set of fundus autofluorescence (FAF) images of a retina. The retina may belong to a subject that has been diagnosed with geographic atrophy or, in some cases, a precursor stage to geographic atrophy. The set of FAF images may include, for example, a single baseline FAF image or multiple baseline FAF images. As described above, a baseline FAF image corresponds to a baseline point in time. When the set of FAF images includes multiple baseline FAF images, these baseline FAF images may all have been generated for the same or substantially same (e.g., within the same hour, within the same day, within the same 1-3 days, etc.) point or points in time.

Step 504 includes generating an input for a machine learning system using the set of FAF images. In some embodiments, step 504 includes sending the set of FAF images directly into the machine learning system as an input. In other embodiments, step 504 may be performed by preprocessing the set of FAF images to form an input. Preprocessing may include resizing each of the set of FAF images to a selected size. The selected size may be, for example, without limitation, 512 pixels by 512 pixels. Preprocessing may include normalizing the image (e.g., pixel) intensities to a selected scale. The selected scale may be, for example, without limitation, 0 to 1, −1 to 1, or some other scale.

Step 506 includes predicting, via the machine learning system, a lesion growth rate for a geographic atrophy lesion in the retina using the input. In some embodiments, the lesion growth rate is an annualized growth rate. Step 506 may be implemented using, for example, GA Prediction NN System 124 of machine learning system 116 in FIG. 1. GA Prediction NN System 124 having base architecture 200 in FIG. 2, multitask architecture 300 in FIG. 3, or cascade architecture 400 in FIG. 4 may be used to perform step 506. With base architecture 200, GA Prediction NN System 124 outputs lesion growth rate 122 from FIGS. 1 and 2. With base architecture 200, GA Prediction NN System 124 provides end-to-end prediction in which the input is automatically processed to predict lesion growth rate 122.

With multitask architecture 300, GA Prediction NN System 124 outputs both lesion growth rate 122 and lesion area 121 from FIGS. 1 and 3. For example, with multitask architecture 300, GA Prediction NN System 124 may output both lesion growth rate 122 and lesion area 121 simultaneously in a multipath approach. With cascade architecture 400, GA Prediction NN System 124 outputs lesion growth rate 122 and lesion area 121 from FIGS. 1 and 4, but in a cascade path approach such that lesion area 121 is predicted first by area subsystem 401, and then used by growth rate subsystem 402 to predict lesion growth rate 122. In other words, with cascade architecture 400, lesion growth rate 122 predicted by growth rate subsystem 402 is dependent on lesion area 121 predicted by area subsystem 401.

With each of these different architectures for GA Prediction NN System 124, GA Prediction NN System 124 can provide end-to-end prediction in which the input is automatically processed to predict lesion growth rate 122 and/or lesion area 121. Human intervention is not needed in the prediction mode. Further, neither scoring of outputs nor feature extraction are needed as intermediate steps.

The machine learning system used in step 506 has been trained using a training dataset (e.g., training dataset 130 in FIG. 1) that ensures lesion area 121 and lesion growth rate 122 are predicted with at least a threshold level accuracy. This threshold level of accuracy for lesion area 121 may be defined based on, for example, a performance metric (e.g., coefficient of determination ($R^2$) computed as the square of the Pearson correlation coefficient). For example, an $R^2$ that is about 0.45 or greater, about 0.48 or greater, or about 0.50 or greater may indicate the desired level of accuracy. The threshold level of accuracy for lesion growth rate 122 may also be defined based on, for example, a performance metric (e.g., coefficient of determination ($R^2$) computed as the square of the Pearson correlation coefficient). For example, an $R^2$ that is about 0.90 or greater, about 0.92 or greater, about 0.94 or greater, or about 0.95 or greater may indicate the desired level of accuracy.

Figure 6:
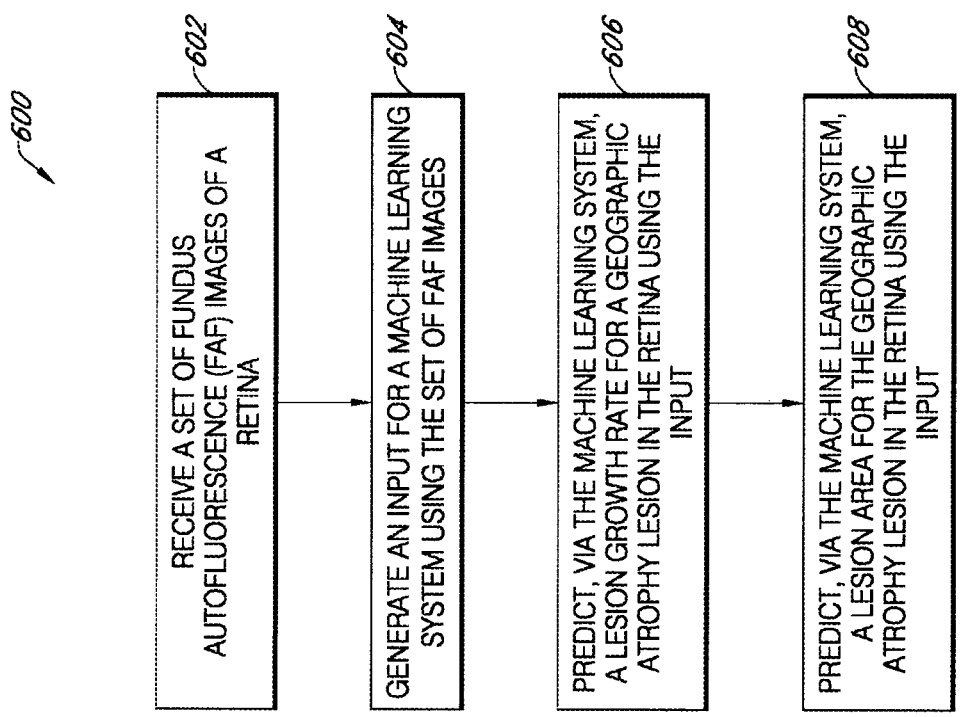
FIG. 6 is a flowchart of a process for evaluating a geographic atrophy lesion in accordance with various embodiments.

FIG. 6 is a flowchart of a process 600 for evaluating a geographic atrophy lesion in accordance with various embodiments. In various embodiments, process 600 is implemented using the lesion evaluation system 100 described in FIG. 1. In particular, process 600 may be implemented using GA Prediction NN System 124 having multitask architecture 300 in FIG. 3 to predict lesion growth rate 122 and lesion area 121.

Step 602 includes receiving a set of fundus autofluorescence (FAF) images of a retina. The retina may belong to a subject that has been diagnosed with geographic atrophy or, in some cases, a precursor stage to geographic atrophy. The set of FAF images may include, for example, a single baseline FAF image or multiple baseline FAF images. As described above, a baseline FAF image corresponds to a baseline point in time. When the set of FAF images includes multiple baseline FAF images, these baseline FAF images may all have been generated for the same or substantially same (e.g., within the same hour, within the same day, within the same 1-3 days, etc.) point or points in time.

Step 604 includes generating an input for a machine learning system using the set of FAF images. In some embodiments, step 604 includes sending the set of FAF images directly into the machine learning system as an input. In other embodiments, step 604 may be performed by preprocessing the set of FAF images to form an input. Preprocessing may include resizing each of the set of FAF images to a selected size. The selected size may be, for example, without limitation, 612 pixels by 612 pixels. Preprocessing may include normalizing the image (e.g., pixel) intensities to a selected scale. The selected scale may be, for example, without limitation, 0 to 1, −1 to 1, or some other scale.

Step 606 includes predicting, via the machine learning system, a lesion growth rate for a geographic atrophy lesion in the retina using the input. In some embodiments, the lesion growth rate, which may be lesion growth rate 122 from FIGS. 1 and 3, is an annualized growth rate.

Step 608 includes predicting, via the machine learning system, a lesion area for a geographic atrophy lesion in the retina using the input. The lesion area, which may be lesion area 121 from FIGS. 1 and 3, may be a baseline lesion area for the baseline point in time or may be a predicted lesion area for a point in time after the baseline point in time.

Steps 606 and 608 may be implemented using, for example, GA Prediction NN System 124 of machine learning system 116 in FIGS. 1 and 3, having multitask architecture 300 in FIG. 3. With multitask architecture 300, GA Prediction NN System 124 is capable of predicting lesion area 121 and lesion growth rate 122 in parallel (e.g., simultaneously). In some embodiments, a multitask architecture takes less time (e.g., half the time) to train as compared to a cascade architecture. Further, the multitask architecture may be less prone to overfitting because the neural network system having such a multitask architecture may be capable of capturing the information from an input that can be used for predicting both lesion area and lesion growth rate.

Figure 7:
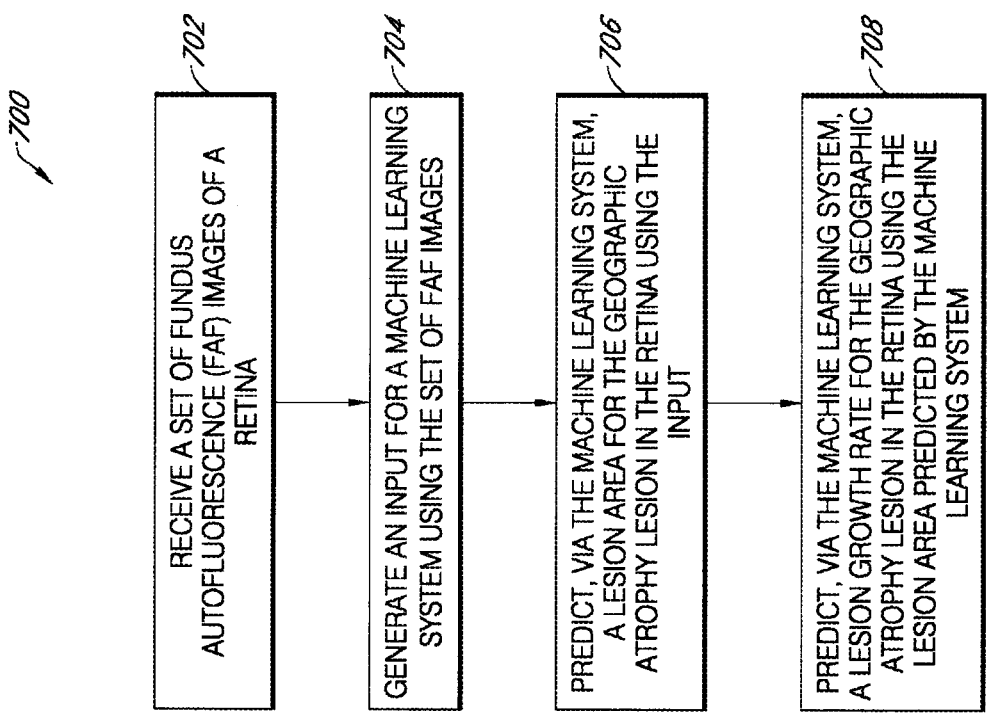
FIG. 7 is a flowchart of a process for evaluating a geographic atrophy lesion in accordance with various embodiments.

FIG. 7 is a flowchart of a process 700 for evaluating a geographic atrophy lesion in accordance with various embodiments. In various embodiments, process 700 is implemented using the lesion evaluation system 100 described in FIG. 1. In particular, process 700 may be implemented using GA Prediction NN System 124 having cascade architecture 400 in FIG. 4 to predict lesion growth rate 122 and lesion area 121.

Step 702 includes receiving a set of fundus autofluorescence (FAF) images of a retina. The retina may belong to a subject that has been diagnosed with geographic atrophy or, in some cases, a precursor stage to geographic atrophy. The set of FAF images may include, for example, a single baseline FAF image or multiple baseline FAF images. As described above, a baseline FAF image corresponds to a baseline point in time. When the set of FAF images includes multiple baseline FAF images, these baseline FAF images may all have been generated for the same or substantially same (e.g., within the same hour, within the same day, within the same 1-3 days, etc.) point or points in time.

Step 704 includes generating an input for a machine learning system using the set of FAF images. In some embodiments, step 704 includes sending the set of FAF images directly into the machine learning system as an input. In other embodiments, step 704 may be performed by preprocessing the set of FAF images to form an input. Preprocessing may include resizing each of the set of FAF images to a selected size. The selected size may be, for example, without limitation, 712 pixels by 712 pixels. Preprocessing may include normalizing the image (e.g., pixel) intensities to a selected scale. The selected scale may be, for example, without limitation, 0 to 1, −1 to 1, or some other scale.

Step 706 includes predicting, via the machine learning system, a lesion area for a geographic atrophy lesion in the retina using the input. The lesion area, which may be lesion area 121 from FIGS. 1 and 4, may be a baseline lesion area for the baseline point in time or may be a predicted lesion area for a point in time after the baseline point in time. Step 706 may be performed by an area subsystem (e.g., area subsystem 401 in FIG. 4) of a neural network system of the machine learning system.

Step 708 includes predicting, via the machine learning system, a lesion growth rate for the geographic atrophy lesion using the lesion area predicted by the machine learning system. In some embodiments, the lesion growth rate, which may be lesion growth rate 122 from FIGS. 1 and 4, is an annualized growth rate. Step 708 may be performed by a growth rate subsystem (e.g., growth rate subsystem 402 in FIG. 4) of the neural network system of the machine learning system. In various embodiments, the growth rate subsystem is trained based on pre-trained parameters (e.g., weights) from the area subsystem. In this manner, the training of the machine learning system occurs in a cascade fashion.

Figure 8:
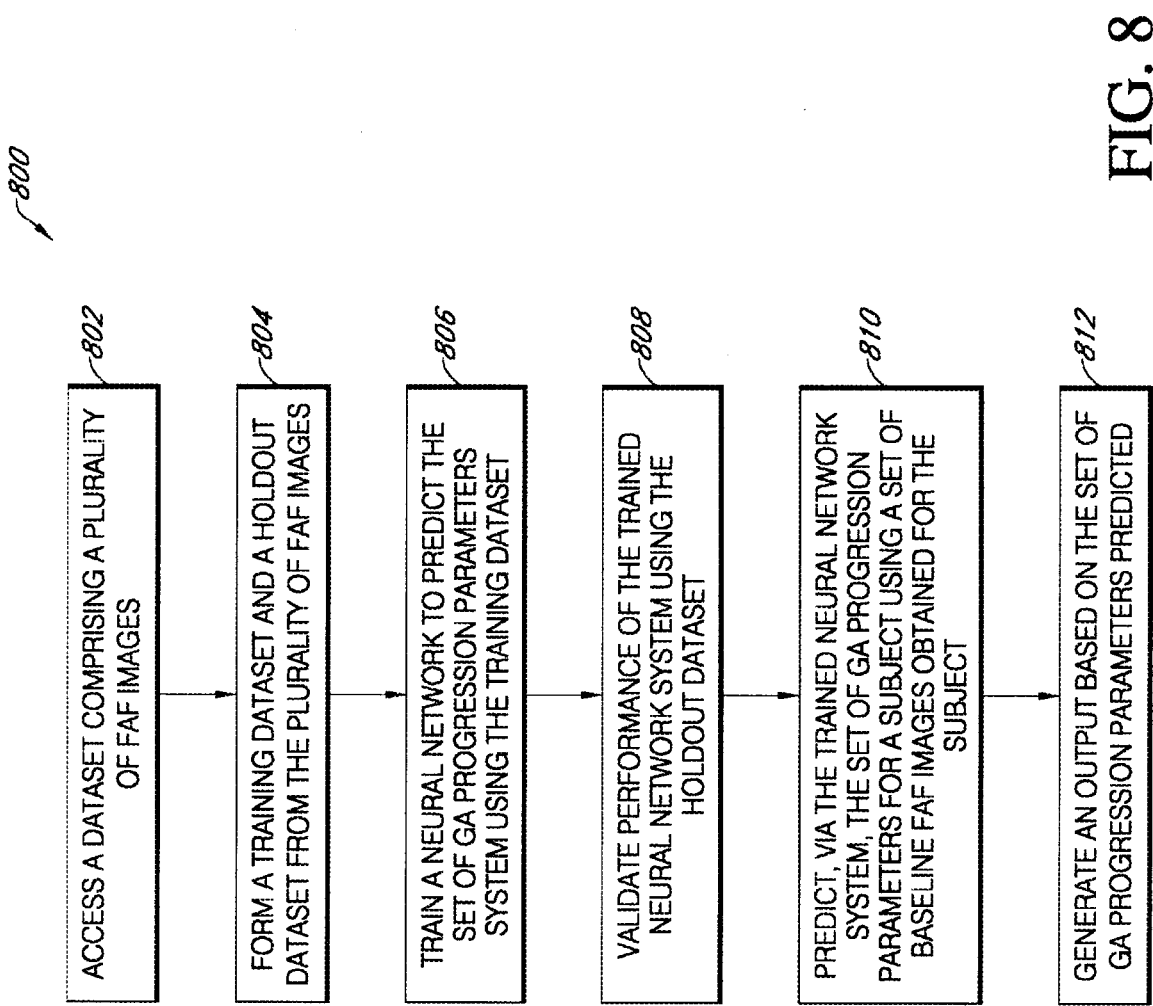
FIG. 8 is a flowchart of a process for predicting a set of GA progression parameters in accordance with various embodiments.

FIG. 8 is a flowchart of a process 800 for predicting a set of GA progression parameters in accordance with various embodiments. Process 800 may be implemented using machine learning system 116 in FIG. 1. For example, process 800 may be implemented using GA Prediction NN System 124 of machine learning system 116 in FIG. 1. In some embodiments, GA Prediction NN System 124 has multitask architecture 300 in FIG. 3 or a similar type of multitask architecture. In other embodiments, GA Prediction NN System 124 has multitask architecture 300 in FIG. 3 or a similar type of multitask architecture.

Step 802 includes accessing a dataset comprising a plurality of FAF images. This dataset may be, for example, accessed from a database, cloud storage, or some other type of storage. The dataset may include FAF images from multiple sources such as, for example, clinical trials or studies. These selected clinical trials or studies have the same (or substantially same or similar) inclusion criteria. The dataset may include FAF images of subjects that have been diagnosed with bilateral geographic atrophy.

Step 804 includes forming a training dataset and a holdout dataset from the plurality of FAF images. For example, without limitation, about 80% of the dataset may be used to form the training dataset, while about 20% of the dataset may be used to form the holdout set. The FAF images selected from the plurality of FAF images for both training and holdout may be baseline FAF images. In some embodiments, step 804 includes preprocessing (e.g., resizing, normalizing) the FAF images. In some embodiments, step 804 includes augmenting or modifying each FAF image selected for training to produce one or more modified FAF images. The original FAF image and the one or more modified images thus form a group of FAF images for training. For example, the original FAF image may be horizontally flipped to form a flipped FAF image, rotated to form a rotated FAF image, adjusted for brightness to form a brightness-adjusted FAF image, and adjusted for contrast to form a contrast-adjusted FAF images. The original FAF image, the flipped FAF image, the rotated FAF image, the brightness-adjusted image, and the contrast-adjusted image may all be added to the training dataset.

Step 806 includes training a neural network to predict the set of GA progression parameters system using the training dataset. The set of GA progression parameters includes lesion area and lesion growth rate. Training may be performed in different ways. When the neural network system has a multitask architecture, training for the prediction of lesion area and lesion growth rate may occur in parallel (e.g., simultaneously). When the neural network system has a cascade architecture with both an area subsystem and a growth rate subsystem, training of the area subsystem for the prediction of lesion area may occur first to identify a first set of parameters for the area subsystem. This first set of parameters may then be used to train the growth rate subsystem for the prediction of lesion growth rate.

Step 808 includes validating performance of the trained neural network system using the holdout dataset. This validation ensures that the neural network system is capable of predicting the set of GA progression parameters with the desired level of accuracy.

Step 810 includes predicting, via the trained neural network system, the set of GA progression parameters for a subject using a set of baseline FAF images obtained for the subject. Step 810 includes predicting lesion area and lesion growth area.

Step 812 includes generating an output based on the set of GA progression parameters predicted. Step 812 may include using at least one GA progression parameter to make a decision or determination. For example, the output generated in step 812 may be a visual output (e.g., a visual alert, a visual notification, a report, etc.), an audible output (e.g., an audible alert, an audible notification, a tone, etc.), or some other type of output that indicates a determination of whether to enroll the subject in a clinical trial, a determination of the dose amount for a first treatment dose, a determination of an interval between doses of a treatment, some other type of clinical determination, or a combination thereof.

Figure 9:
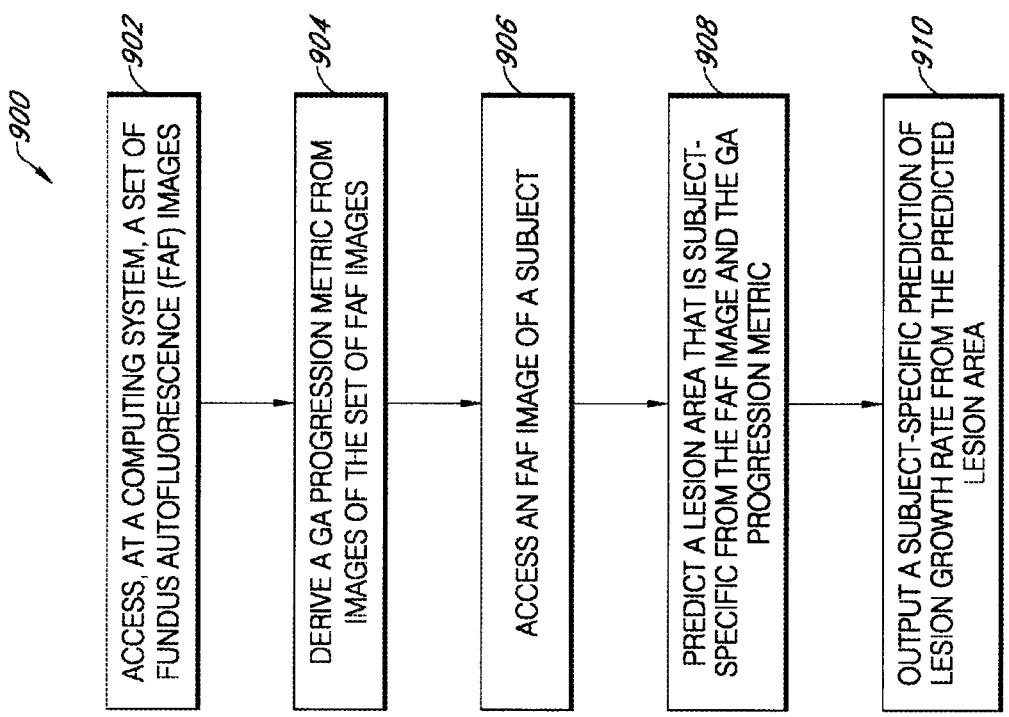
FIG. 9 is a flowchart of a process for predicting a set of GA progression parameters in accordance with various embodiments.

FIG. 9 is a flowchart of a process 900 for predicting a set of GA progression parameters in accordance with various embodiments. In various embodiments, process 800 may be implemented using machine learning system 116 in FIG. 1. For example, process 800 may be implemented using GA Prediction NN System 124 of machine learning system 116 in FIG. 1.

Step 902 includes accessing, at a computing system, a set of fundus autofluorescence (FAF) images. The computing system may be, for example, computing platform 102 in FIG. 1 or computer system 1400 in FIG. 14 below. The set of FAF images may include FAF images generated for one or more subjects at different visits. For a given subject, the set of FAF images may include a baseline FAF image for a baseline visit and the FAF image from at least one follow-up visit of the subject.

Step 904 includes deriving a GA progression metric from images of the set of FAF images. The GA progression metric may be, for example, a lesion growth rate. Step 904 may be performed by, for example, fitting a linear model to estimated lesion area measurements for each subject.

Step 906 includes accessing an FAF image of a subject. The FAF image accessed in step 906 may be a baseline FAF image for the subject.

Step 908 includes predicting a lesion area that is subject-specific from the FAF image and the GA progression metric. Step 908 may be performed using deep learning. The lesion area may be predicted for some future point in time (e.g., 6 months, one year, or two years after the baseline point in time).

Step 910 includes outputting a subject-specific prediction of lesion growth rate from the predicted lesion area. Step 910 may be performed using deep learning.

III. Examples/Results

Figure 10:
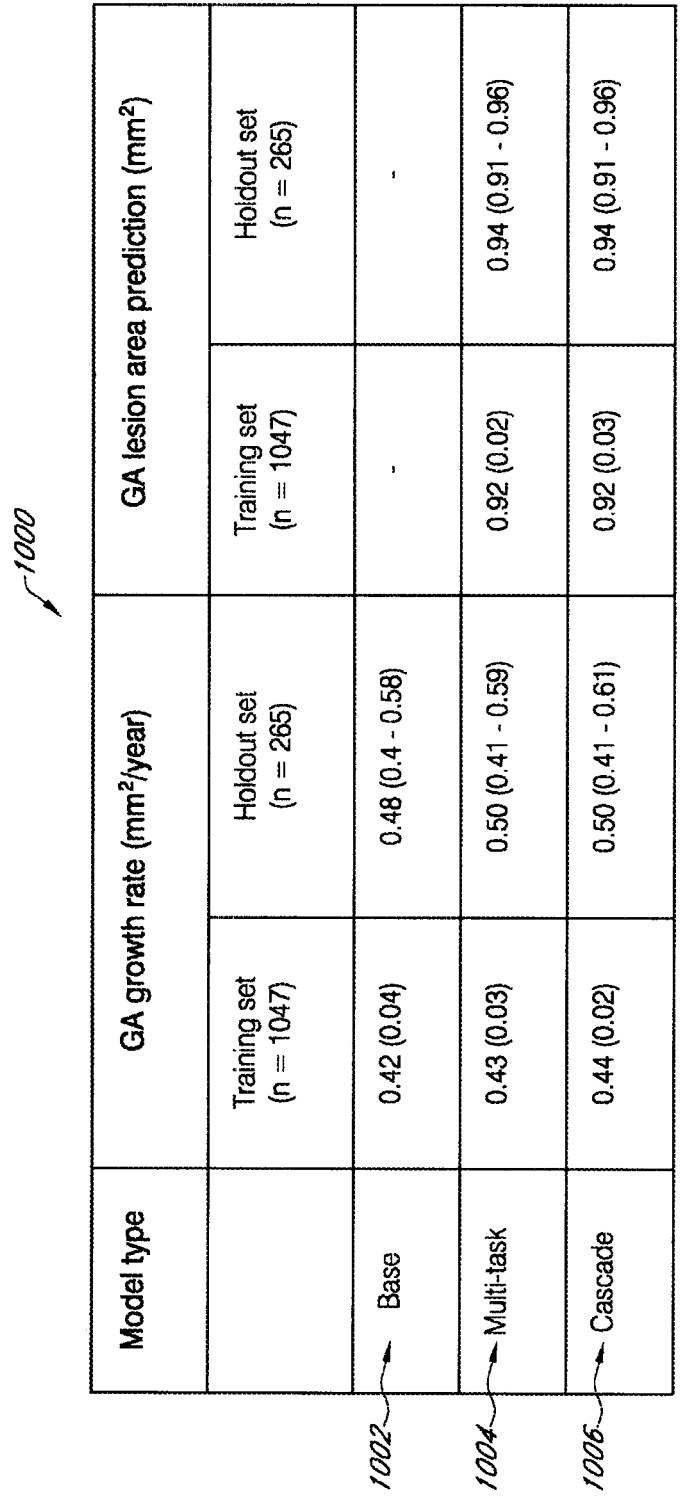
FIG. 10 is a table illustrating the performance of three different types of machine learning models in accordance with various embodiments.

FIG. 10 is a table illustrating the performance of three different types of machine learning models in accordance with various embodiments. Table 1000 illustrates the post-training performance of base model 1002 that has a deep learning neural network system with a base architecture such as base architecture 200 in FIG. 2, multitask model 1004 that has a deep learning neural network system with a multitask architecture such as multitask architecture 300 in FIG. 3, and cascade model 1006 that has a deep learning neural network system with a cascade architecture such as cascade architecture 400 in FIG. 4.

Base model 1002, multitask model 1004, and cascade model 1006 were trained using a training dataset developed from baseline FAF images obtained from three separate clinical trials for a selected GA treatment. These three clinical trials adhered to the tenets of the Declaration of Helsinki and were Health Insurance Portability and Accountability Act compliant. The protocol for each clinical trial included using the same inclusion criteria used to enroll subjects in the clinical trials. All subjects enrolled in the clinical trials had diagnoses of bilateral GA.

The FAF images captured in the three clinical trials were macula-centered 30-degree FAF images having a size of 768 pixels by 768 pixels. FAF images were captured for each subject every 24 weeks within a two-year range. Lesion area ($mm^2$) was determined for each visit by human graders (e.g., trained experts and, in some cases, involving an adjudicator). Lesion growth rate ($mm^2$/year) was derived from a linear model fitted to the lesion area measurements over the two years. The lesion growth rate across the three clinical trials for the two years ranged from 0.15 $mm^2$/year to 5.98 $mm^2$/year. The lesion area across the three clinical trials over the two years ranged from 2.54 $mm^2$ to 17.78 $mm^2$.

In this example study, the baseline FAF images of 1312 subjects from the three clinical trials was used, with the baseline FAF images for 1047 subjects being used for the training dataset and the baseline FAF images for 265 subjects being used for the holdout dataset for model tuning. The training dataset was further divided into 5 folds for cross-validation, with the splits being balanced for baseline factors (e.g., gender, lesion area, lesion growth rate, fovea involvement, lesion contiguity, multifocality, best corrected visual acuity (BCVA) measurements, and low luminance deficit).

In the example study, prior to training and model tuning, the baseline FAF images were preprocessed. The baseline FAF images were resized to 512 pixels by 512 pixels. The image (e.g., pixel) intensities were normalized to a scale between 0 and 1. This resizing and normalization were selected to improve the performance of each of the three models being evaluated. In this example study, preprocessing further included augmenting the training dataset. For example, each baseline FAF image in the training dataset was horizontally flipped, rotated (e.g., between about −5 degrees and 5 degrees), adjusted for random brightness, adjusted for random contrast to produce four additional baseline FAF images. Thus, for each subject, a total of five baseline FAF images (the original and the four modified) were used for training. Such augmentation was not performance for the baseline FAF images of the holdout dataset.

Tuning of the model hyperparameters was performed using a 5-fold cross validation (CV) approach. After the model hyper-parameters were selected, each model was retrained on the full training dataset and then used to predict on the holdout dataset. The training performance of the three models shown in table 1000 is given $R^2$ of the 5 folds and the holdout performance is given as $R^2$. As shown in table 1000, on the training dataset, cascade model 1006 performed better than base model 1002 and multitask model 1004 for predicting lesion growth rate. On the holdout dataset, both cascade model 1006 and multitask model 1004 had similar performance that was better than that of base model 1002 for predicting both lesion growth rate. For lesion area, both cascade model 1006 and multitask model 1004 had similar performance for both the training dataset and the holdout dataset.

Figure 11:
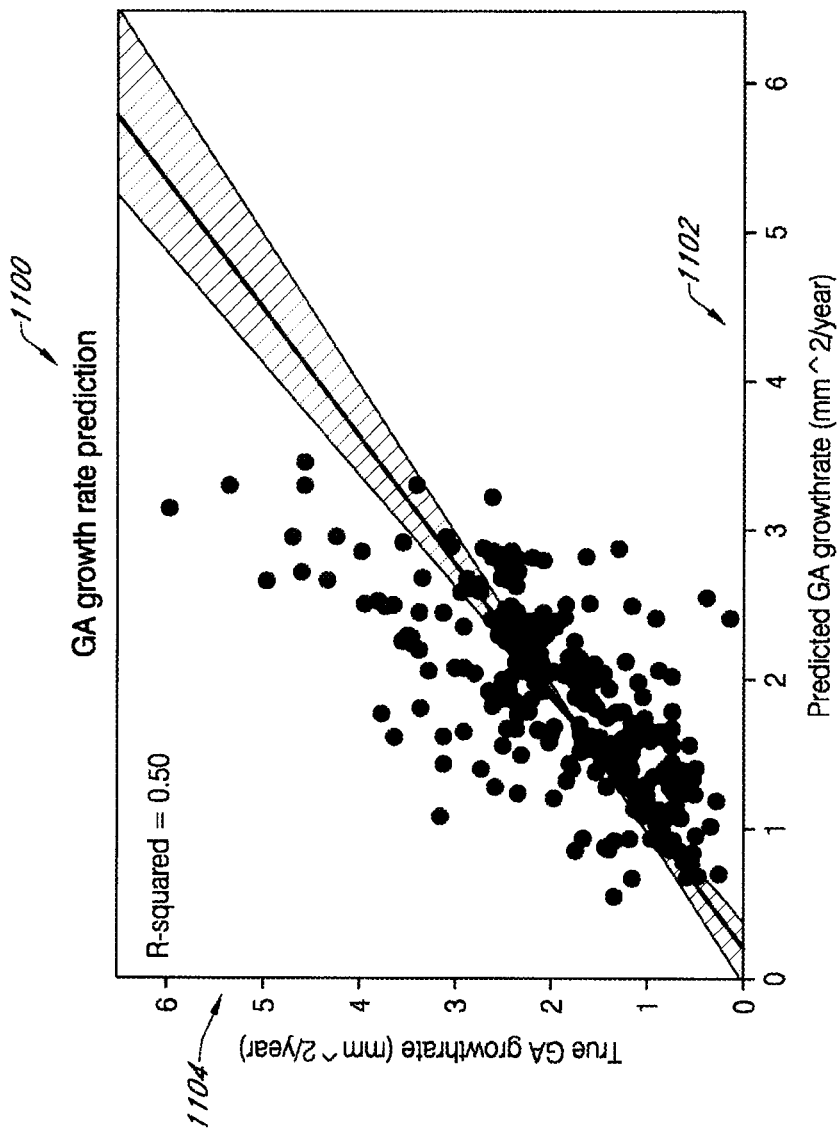
FIG. 11 is a regression plot diagram of predicted lesion growth rate versus true lesion growth rate in accordance with various embodiments.

FIG. 11 is a regression plot diagram of predicted lesion growth rate versus true lesion growth rate in accordance with various embodiments. Plot 1100 has x-axis 1102 corresponding to predicted lesion growth rate and y-axis 1104 corresponding to true lesion growth rate. Plot 1100 is a scatter plot showing the predicted lesion growth rate versus the true lesion growth rate for the holdout set using the multitask model 1004 of FIG. 10.

Figure 12:
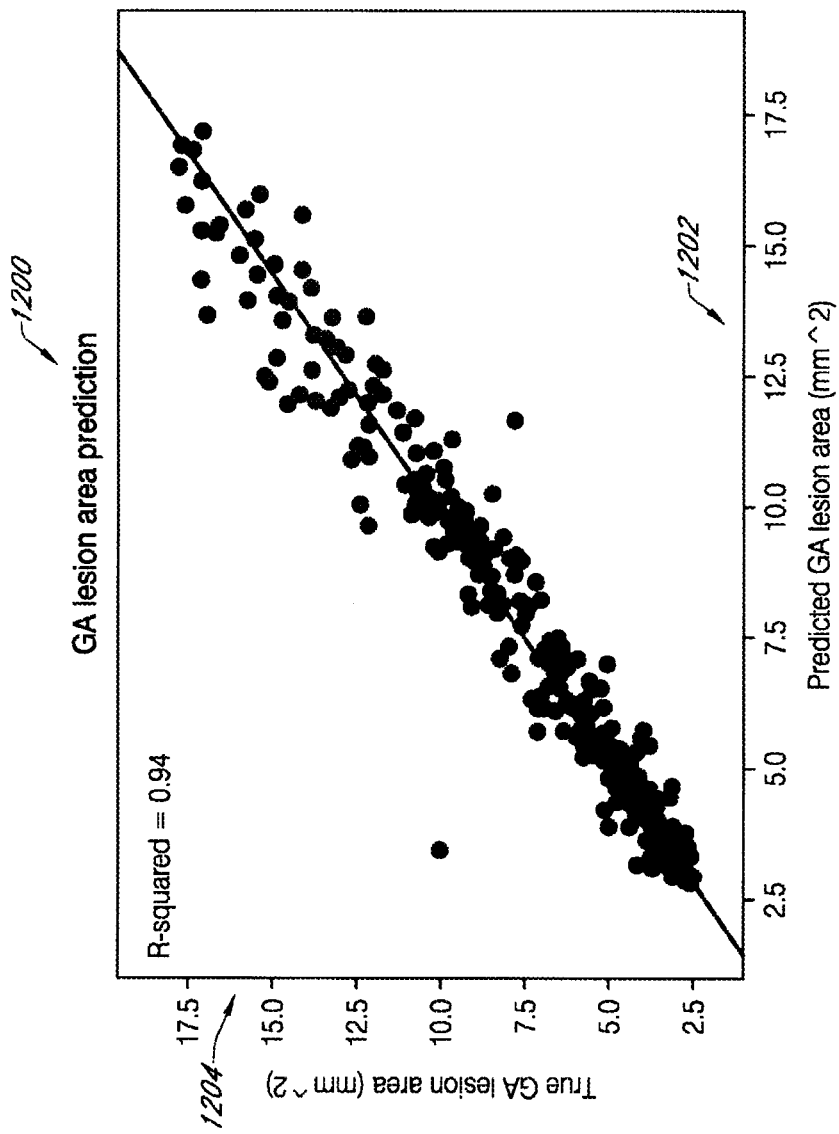
FIG. 12 is a regression plot diagram of predicted lesion area versus true lesion area in accordance with various embodiments.

FIG. 12 is a regression plot diagram of predicted lesion area versus true lesion area in accordance with various embodiments. Plot 1200 has x-axis 1202 corresponding to predicted lesion area and y-axis 1204 corresponding to true lesion area. Plot 1200 is a scatter plot showing the predicted lesion area versus the true lesion area for the holdout set using the multitask model 1004 of FIG. 10.

FIG. 13 is a table illustrating the training performance of a multitask model in predicting both lesion growth rate and lesion area in accordance with various embodiments. The multitask model is a machine learning model that includes a neural network system having a multitask architecture such as, for example, multitask architecture 300 in FIG. 3. Performance on the holdout set for the same multitask model evaluated in FIG. 13 was an $R^2$ of 0.96 for lesion area prediction and an $R^2$ of 0.48 (range 0.41-0.55) for lesion growth rate.

IV. Computer Implemented System

Figure 14:
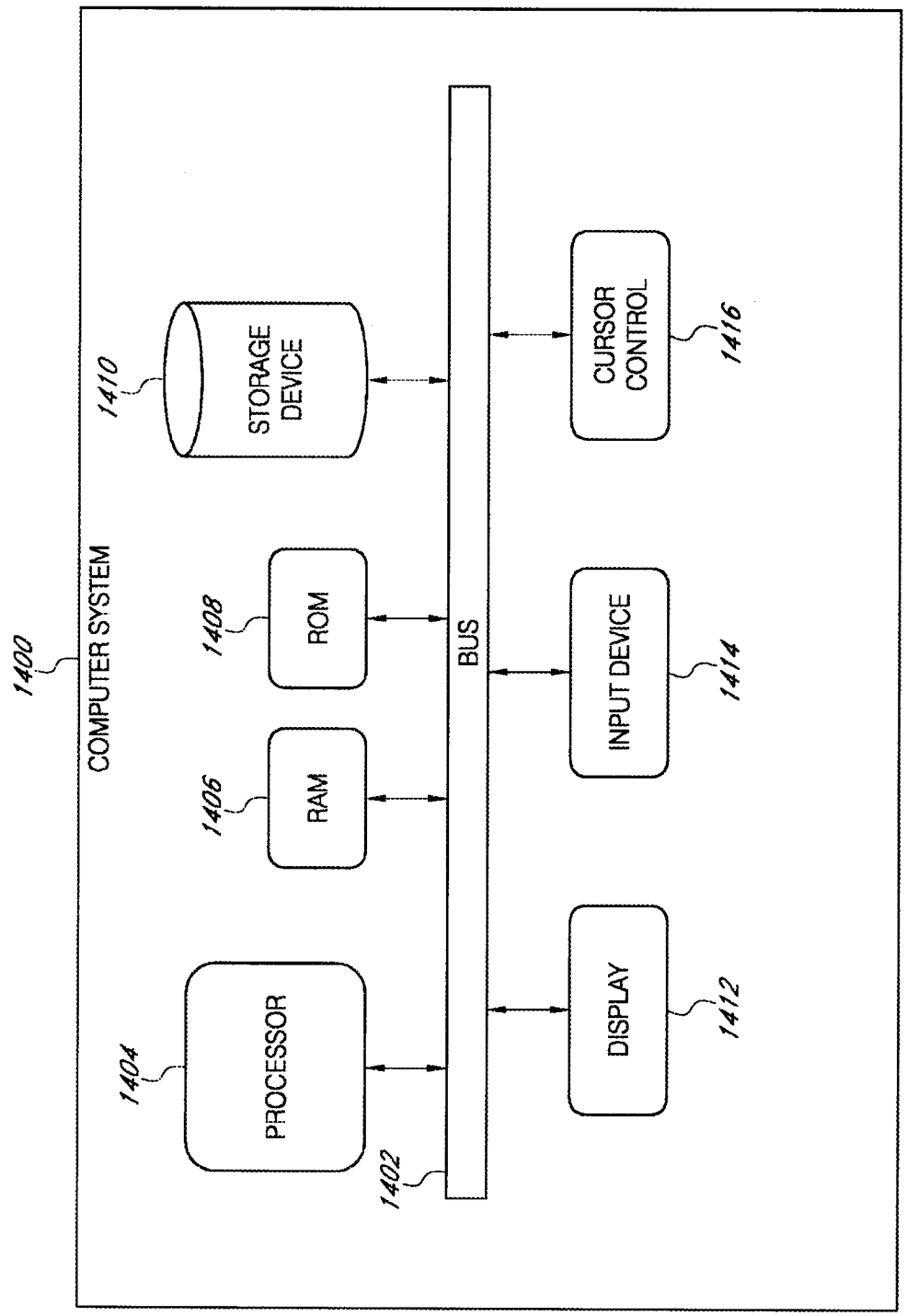
FIG. 14 is a block diagram of a computer system in accordance with various embodiments.

FIG. 14 is a block diagram of a computer system in accordance with various embodiments. Computer system 1400 may be an example of one implementation for computing platform 102 described above in FIG. 1.

In one or more examples, computer system 1400 can include a bus 1402 or other communication mechanism for communicating information, and a processor 1404 coupled with bus 1402 for processing information. In various embodiments, computer system 1400 can also include a memory, which can be a random-access memory (RAM) 1406 or other dynamic storage device, coupled to bus 1402 for determining instructions to be executed by processor 1404. Memory also can be used for storing temporary variables or other intermediate information during execution of instructions to be executed by processor 1404. In various embodiments, computer system 1400 can further include a read only memory (ROM) 1408 or other static storage device coupled to bus 1402 for storing static information and instructions for processor 1404. A storage device 1410, such as a magnetic disk or optical disk, can be provided and coupled to bus 1402 for storing information and instructions.

In various embodiments, computer system 1400 can be coupled via bus 1402 to a display 1412, such as a cathode ray tube (CRT) or liquid crystal display (LCD), for displaying information to a computer user. An input device 1414, including alphanumeric and other keys, can be coupled to bus 1402 for communicating information and command selections to processor 1404. Another type of user input device is a cursor control 1416, such as a mouse, a joystick, a trackball, a gesture input device, a gaze-based input device, or cursor direction keys for communicating direction information and command selections to processor 1404 and for controlling cursor movement on display 1412. This input device 1414 typically has two degrees of freedom in two axes, a first axis (e.g., x) and a second axis (e.g., y), that allows the device to specify positions in a plane. However, it should be understood that input devices 1414 allowing for three-dimensional (e.g., x, y, and z) cursor movement are also contemplated herein.

Consistent with certain implementations of the present teachings, results can be provided by computer system 1400 in response to processor 1404 executing one or more sequences of one or more instructions contained in RAM 1406. Such instructions can be read into RAM 1406 from another computer-readable medium or computer-readable storage medium, such as storage device 1410. Execution of the sequences of instructions contained in RAM 1406 can cause processor 1404 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 1404 for execution. Such a medium can take many forms, including but not limited to, non-volatile media, volatile media, and transmission media. Examples of non-volatile media can include, but are not limited to, optical, solid state, magnetic disks, such as storage device 1410. Examples of volatile media can include, but are not limited to, dynamic memory, such as RAM 1406. Examples of transmission media can include, but are not limited to, coaxial cables, copper wire, and fiber optics, including the wires that comprise bus 1402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 1404 of computer system 1400 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 1400 as a standalone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1400, whereby processor 1404 would execute the analyses and determinations provided by these engines, subject to instructions provided by any one of, or a combination of, the memory components RAM 1406, ROM, 1408, or storage device 1410 and user input provided via input device 1414.

V. Exemplary Definitions

The disclosure is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology, and toxicology are described herein are those well-known and commonly used in the art.

As the terms "on," "attached to," "connected to," "coupled to," or similar words are used herein, one element (e.g., a component, a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

The term "subject" may refer to a subject of a clinical trial, a person undergoing treatment, a person undergoing anti-cancer therapies, a person being monitored for remission or recovery, a person undergoing a preventative health analysis (e.g., due to their medical history), or any other person or patient of interest. In various cases, "subject" and "patient" may be used interchangeably herein.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" may be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, a "model" may include one or more algorithms, one or more mathematical techniques, one or more machine learning algorithms, or a combination thereof.

As used herein, "machine learning" may be the practice of using algorithms to parse data, learn from it, and then make a determination or prediction about something in the world. Machine learning uses algorithms that can learn from data without relying on rules-based programming.

As used herein, an "artificial neural network" or "neural network" (NN) may refer to mathematical algorithms or computational models that mimic an interconnected group of artificial nodes or neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network may process information in two ways: when it is being trained it is in training mode and when it puts what it has learned into practice it is in inference (or prediction) mode. Neural networks learn through a feedback process (e.g., backpropagation) which allows the network to adjust the weight factors (modifying its behavior) of the individual nodes in the intermediate hidden layers so that the output matches the outputs of the training data. In other words, a neural network learns by being fed training data (learning examples) and eventually learns how to reach the correct output, even when it is presented with a new range or set of inputs. A neural network may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), or another type of neural network.

As used herein, a "lesion" may be a region in an organ or tissue that has suffered damage via injury or disease. This region may be a continuous or discontinuous region. For example, as used herein, a lesion may include multiple regions. A geographic atrophy (GA) lesion is a region of the retina that has suffered chronic progressive degeneration. As used herein, a GA lesion may include one lesion (e.g., one continuous lesion region) or multiple lesions (e.g., discontinuous lesion region comprised of multiple, separate lesions).

As used herein, a "lesion area" may be the total area covered by a lesion, whether that lesion be a continuous region or a discontinuous region.

As used herein, "longitudinal" may refer to over a period of time. The period of time may be in days, weeks, months, years, or some other measure of time.

As used herein, a "growth rate" corresponding to a GA lesion may be a longitudinal change in the lesion area of the GA lesion. In other words, the "growth rate" may be a change in lesion area over time. In some cases, this growth rate may be an annualized growth rate. This growth rate may also be referred to as a lesion growth rate or a GA growth rate.

VI. Additional Considerations

Any headers and/or subheaders between sections and subsections of this document are included solely for the purpose of improving readability and do not imply that features cannot be combined across sections and subsection. Accordingly, sections and subsections do not describe separate embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art. The present description provides preferred exemplary embodiments, and is not intended to limit the scope, applicability, or configuration of the disclosure. Rather, the present description of the preferred exemplary embodiments will provide those skilled in the art with an enabling description for implementing various embodiments. It is understood that various changes may be made in the function and arrangement of elements without departing from the spirit and scope as set forth in the appended claims. Thus, such modifications and variations are considered to be within the scope set forth in the appended claims. Further, the terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

Specific details are given in the present description to provide an understanding of the embodiments. However, it is understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method for evaluating geographic atrophy in a retina, the method comprising:
   receiving a set of fundus autofluorescence (FAF) images of the retina;
   generating an input for a machine learning system using the set of fundus autofluorescence images;
   predicting, via the machine learning system, a lesion area for a geographic atrophy lesion in the retina using the set of fundus autofluorescence images; and
   predicting, via the machine learning system, a lesion growth rate for the geographic atrophy lesion in the retina using the input.

2. The method of claim 1, wherein the set of fundus autofluorescence images comprises a baseline fundus autofluorescence image of the retina corresponding to a baseline point in time and wherein the lesion growth rate is predicted for a point in time after the baseline point in time.

3. The method of claim 1, wherein the set of fundus autofluorescence images comprises a baseline fundus autofluorescence image of the retina corresponding to a baseline point in time and wherein the lesion area is predicted for a point in time after the baseline point in time.

4. The method of claim 1, wherein the generating comprises:
   preprocessing the set of fundus autofluorescence images to form the input for the machine learning system.

5. The method of claim 4, wherein the preprocessing comprises:
   resizing each fundus autofluorescence image of the set of fundus autofluorescence images to a selected size to form the input for the machine learning system.

6. The method of claim 4, wherein the preprocessing comprises:
   normalizing image intensities of each fundus autofluorescence image of the set of fundus autofluorescence images with respect to a selected scale to form the input for the machine learning system.

7. The method of claim 1, wherein predicting, via the machine learning system, the lesion growth rate comprises:
   generating, via a convolutional neural network layer of the machine learning system, a first output based on the input;
   generating, via a pooling layer of the machine learning system, a second output using the first output; and
   predicting, via a dense layer of the machine learning system, the lesion growth rate for the geographic atrophy lesion using the second output.

8. The method of claim 1, wherein predicting, via the machine learning system, the lesion area comprises:
   generating, via a convolutional neural network layer of the machine learning system, a first output based on the input;
   generating, via a pooling layer of the machine learning system, a second output using the first output; and
   predicting, via a dense layer of the machine learning system, the lesion area for the geographic atrophy lesion using the second output.

9. The method of claim 1, further comprising:
   training the machine learning system using a plurality of fundus autofluorescence images obtained from a plurality of clinical studies having same inclusion criteria.

10. The method of claim 1, wherein the machine learning system comprises a deep learning neural network system.

11. A method for evaluating geographic atrophy in a retina, the method comprising:
    receiving a set of fundus autofluorescence (FAF) images of the retina;
    generating an input for a machine learning system using the set of fundus autofluorescence images;
    predicting, via the machine learning system, a lesion area for a geographic atrophy lesion in the retina using the input; and
    predicting, via the machine learning system, a lesion growth rate for the geographic atrophy lesion using the lesion area predicted by the machine learning system.

12. The method of claim 11, wherein the set of fundus autofluorescence images comprises a baseline fundus autofluorescence image of the retina corresponding to a baseline point in time and wherein the lesion growth rate is predicted for a point in time after the baseline point in time.

13. The method of claim 11, wherein the set of fundus autofluorescence images comprises a baseline fundus autofluorescence image of the retina corresponding to a baseline point in time and wherein the lesion area is predicted for a point in time after the baseline point in time.

14. The method of claim 11, wherein the generating comprises:
    preprocessing the set of fundus autofluorescence images to form the input for the machine learning system.

15. The method of claim 14, wherein the preprocessing comprises at least one of:
    resizing each fundus autofluorescence image of the set of fundus autofluorescence images to a selected size to form the input for the machine learning system; or
    normalizing image intensities of each fundus autofluorescence image of the set of fundus autofluorescence images with respect to a selected scale to form the input for the machine learning system.

16. The method of claim 11, wherein the machine learning system comprises a neural network system that uses deep learning and further comprising:
    training an area subsystem of the neural network system to predict lesion area; and
    training a growth rate subsystem of the machine learning system to predict lesion growth rate using a set of pre-trained parameters identified from training the area subsystem.

17. A system comprising:
    one or more data processors; and a non-transitory computer readable storage medium containing instructions which, when executed on the one or more data processors, cause the one or more data processors to:
  receive a set of fundus autofluorescence (FAF) images of the retina;
  generate an input for a machine learning system using the set of fundus autofluorescence images;
  predict, via the machine learning system, a lesion area for a geographic atrophy lesion in the retina using the set of fundus autofluorescence images; and
  predict, via the machine learning system, a lesion growth rate for the geographic atrophy lesion in the retina using the input.

18. The system of claim 17, wherein the set of fundus autofluorescence images comprises a baseline fundus autofluorescence image of the retina corresponding to a baseline point in time and wherein the lesion growth rate is predicted for a point in time after the baseline point in time.

19. The system of claim 17, wherein the set of fundus autofluorescence images comprises a baseline fundus autofluorescence image of the retina corresponding to a baseline point in time and wherein the lesion area is predicted for a point in time after the baseline point in time.

20. The system of claim 17, wherein the instructions, when executed on the one or more data processors, cause the one or more data processors to generate the input by at least one of:
  resize each fundus autofluorescence image of the set of fundus autofluorescence images to a selected size to form the input for the machine learning system; or
  normalize image intensities of each fundus autofluorescence image of the set of fundus autofluorescence images with respect to a selected scale to form the input for the machine learning system.

* * * * *